US011464566B2

(12) United States Patent
Kerbage et al.

(10) Patent No.: US 11,464,566 B2
(45) Date of Patent: *Oct. 11, 2022

(54) SYSTEM AND METHOD FOR LASER BASED TREATMENT OF SOFT TISSUE

(71) Applicant: Convergent Dental, Inc., Needham, MA (US)

(72) Inventors: Charles Kerbage, Arlington, MA (US); Ali Badreddine, Boston, MA (US); Stephen Couitt, Auburndale, MA (US); Steve Miller, West Newbury, MA (US); Nenad Jelisavcic, Groton, MA (US)

(73) Assignee: Convergent Dental, Inc., Needham, MA (US)

( * ) Notice: Subject to any disclaimer, the term of this patent is extended or adjusted under 35 U.S.C. 154(b) by 31 days.

This patent is subject to a terminal disclaimer.

(21) Appl. No.: 17/173,792

(22) Filed: Feb. 11, 2021

(65) Prior Publication Data

US 2021/0353358 A1   Nov. 18, 2021

Related U.S. Application Data

(63) Continuation of application No. 16/993,991, filed on Aug. 14, 2020, now Pat. No. 10,945,790.
(Continued)

(51) Int. Cl.
*A61B 18/00* (2006.01)
*A61B 18/20* (2006.01)
(Continued)

(52) U.S. Cl.
CPC ............ *A61B 18/20* (2013.01); *H01S 3/0071* (2013.01); *H01S 3/2232* (2013.01);
(Continued)

(58) Field of Classification Search
None
See application file for complete search history.

(56) References Cited

U.S. PATENT DOCUMENTS 8,709,057 B2 *   4/2014   Tettamanti   ........... A61N 5/0603
                                                        606/9
10,945,790 B2 *  3/2021   Kerbage   ............... A61B 18/20
(Continued)

FOREIGN PATENT DOCUMENTS

RU            2652072 C1      4/2018

OTHER PUBLICATIONS

Cetinkaya et al., "Er:Yag Laser Treatment of Simple Snorers in an Outpatient Setting," ORL 78:70-76 (2016).
(Continued)

*Primary Examiner* — John R Downey
*Assistant Examiner* — Anant A Gupta
(74) *Attorney, Agent, or Firm* — Goodwin Procter LLP

(57) ABSTRACT

The disclosed invention relates to an improved system and method for treatment of soft tissue, e.g., for treatment of a snoring condition. The system can include a laser source; a hand piece; and a device for directing radiation emitted by the laser source to a treatment area (e.g., an oral treatment area). In some cases, the handpiece can include an optical element (e.g., a lens) mounted within a replaceable cartridge and adapted to modulate a laser beam such that it is non-ablative, prior to its delivery to a treatment region. In various embodiments, the system includes a CO2 laser capable of performing treatment in a more efficient manner than conventional techniques.

20 Claims, 10 Drawing Sheets

Related U.S. Application Data

(60) Provisional application No. 62/887,949, filed on Aug. 16, 2019.

(51) Int. Cl.
*H01S 3/00* (2006.01)
*H01S 3/223* (2006.01)
*A61B 17/00* (2006.01)

(52) U.S. Cl.
CPC ........... *A61B 2017/0019* (2013.01); *A61B 2018/00327* (2013.01); *A61B 2018/00577* (2013.01); *A61B 2018/20355* (2017.05)

(56) References Cited

U.S. PATENT DOCUMENTS

| | | |
|---|---|---|
| 2007/0265606 A1 | 11/2007 | DeBenedictis et al. |
| 2012/0179229 A1 | 7/2012 | Tettamanti et al. |
| 2013/0096546 A1 | 4/2013 | Mirkov et al. |
| 2014/0018783 A1* | 1/2014 | Modi ............ A61N 1/0472 606/9 |
| 2014/0363784 A1 | 12/2014 | Monty et al. |
| 2016/0143703 A1 | 5/2016 | Monty et al. |
| 2017/0172661 A1 | 6/2017 | Ozer Armon et al. |
| 2017/0319277 A1 | 11/2017 | Cantor-Balan et al. |
| 2018/0126190 A1 | 5/2018 | Aviad et al. |

OTHER PUBLICATIONS

Dovsak et al., "NightLase™—a New Laser Treatment Method for the Reduction of Snoring and Sleep Apnea—a Pilot Study (Summary)," J. Laser Health Acad., 1 :S09-S10 (2011).
Fitzpatrick et al., "Collagen Tightening Induced by Carbon Dioxide Laser Versus Erbium: YAG Laser," Lasers in Surgery and Medicine 27:395-403 (2003).
Fiz et al., "Treatment of Patients with Simple Snoring," Arch Bronconeumol 45:508-515 (2009).
Goktas et al., "Biomedical Behavior of Oral Soft Tissues," J. Periodontol 82(8):1178-1186 (2011).
International Search Report and Written Opinion in PCT/US2020/046333, dated Nov. 9, 2020 14 pages.
Jovanovic, J., "NightLase™—Laser-Assisted Snoring and Apnea Reduction, 9 Months of Experience (Summary)," J. Laser Health Acad. (1):S11 (2011).
Kamami, Y.V., "Laser CO2 for Snoring, Preliminary Results," Acata Otorhinolaryngol Belg. 44:451-456 (1990).
Kirsch et al., "Ultrastructure of Collagen Thermally Denatured by Microsecond Domain Pulsed Carbon Dioxide Laser," Arch. Dermatol. 134; 1255-1259 (1998).
Lee et al., "Evaluation of a Non-ablative Er: YAG Laser Procedure to Increase the Oropharyngeal Airway Volume: A Pilot Study," Dental, Oral and Craniofacial Research 1:56-59 (2015).
Lippert et al., "Wound Healing after Laser Treatment of Oral and Oropharyngeal Cancer," Lasers Med. Sci. 18:36-42 (2003).
Maeder et al., "A Clinical Approach to Obstructive Sleep Apnea as a Risk Factor for Cardiovascular Disease," Vascular Health and Risk Management 12:85-103 (2016).
Majaron et al., "Deep Coagulation of Dermal Collagen with Repetitive: Er: YAG Laser Irradiation," Lasers in Surgery and Medicine 26:215-222 (2000).
Miracki et al., "Nonsurgical Minimally Invasive Er:YAG Laser Snoring Treatment," J. of Laser and Health Academy 1:36-41 (2013).
Sippus et al., "Case Report: NightLase® Procedure—Laser Snoring and Sleep Apnea Reduction Treatment," J. Laser and Health Academy 1-5 (2015).
Svahnström, K., "Er:YAG Laser Treatment of Sleep-Disordered Breathing," J. Laser and Health Academy 2:13-16 (2013).
Unver et al., "Histological Effects of NightLase® in the Soft Palate of Rats: A Pilot Study," J. Laser and Health Academy 1-3 (2015).
Von Den Hoff et al., "Palatal Wound Healing: The Effects of Scarring on Growth," Chapter 14.
Wang et al., "Laser Soft Palate "Stiffening"; An Alternative to Uvulpalatopharngoplasty," Lasers in Surgery and Medicine 30:40-43 (2002).
Wehrhan et al., "Salient Features of the Oral Mucosa," Essential Tissue Healing of the Face and Neck pp. 83-99.

* cited by examiner

1: Handpiece
10: Integrated Tongue Depressor

| Soft Tissue Contraction - Parameter Chart | | | | |
|---|---|---|---|---|
| Feature | Min. Value | Nominal value | Max. Value | Unit |
| Wavelength | 9 | 9.3 | 11 | microns |
| Pulse energy | 0.3 | 5 | 6.3 | mJ |
| Pulse duration | 1 | 12 | 30 | μsec |
| Pule repetition rate | 0.05 | 0.315 | 1 | kHz |
| Duty cycle | 0.01 | 0.6 | 5 | % |
| Fluence per pulse | 0.1 | 0.16 | 0.2 | J/cm^2 |
| Power | 1 | 1.5 | 5 | W |
| Number of locations in pattern | 0.01 | 37 | 100 | |
| Total pattern time | 0.01 | 0.118 | 0.5 | sec |
| Total treatment time | 0.1 | 2 | 120 | sec |
| Rate of treatment | 1 / 120 | 1 / 1.8 | 1 / 0.1 | cm^2 / sec |
| Working range | 0.1 | 3 | 10 | cm |
| Pulse delivery rate | 0.1 | 3.2 | 10 | msec/pulse |
| Percentage stiffness increase of lased tissue vs. unlased tissue | 1.1-fold | 25-fold | 250-fold | |
| Percentage stiffness increase of lased tissue immediately after treatment vs. 1 month after treatment | 1.1-fold | 2-fold | 10-fold | |
| Percentage histopathological value increase of lased tissue vs. unlased tissue | 1.1-fold | 25-fold | 250-fold | |
| Percentage histopathological value increase of lased tissue immediately after treatment vs. 1 month after treatment | 1.02-fold | 1.1-fold | 10-fold | |

FIGURE 7

SYSTEM AND METHOD FOR LASER BASED TREATMENT OF SOFT TISSUE

CROSS-REFERENCE TO RELATED APPLICATIONS

This application is a continuation of U.S. patent application Ser. No. 16/993,991, filed on Aug. 14, 2020 and claims the benefit of priority to U.S. Provisional Patent Application No. 62/887,949 entitled "System and Method for Laser Based Treatment of Soft Tissue," filed on Aug. 16, 2019, the contents of which are incorporated herein by reference in their entireties.

FIELD OF THE INVENTION

The present invention generally relates to the treatment of soft tissue using a light-emitting device (e.g., a laser source) and, more particularly, to contracting and stiffening of soft tissue by directing radiation emitted by a laser source to a treatment area, e.g., to treat a snoring condition.

BACKGROUND OF THE INVENTION

Snoring is a very common and generally undesirable form of Sleep-Disordered Breathing (SDB) which affects more than 30% of the adult population and a comparable percentage of children and adolescents. The sound of snoring is usually a consequence of the vibration of pharyngeal soft tissue caused by a partial upper airway collapse during sleep. Snoring can cause sleep deprivation for both snorers and those around them and patients can suffer from severe issues that can lead to heart attack and stroke. [Ref: *A clinical approach to obstructive sleep apnea as a risk factor for cardiovascular disease, Vasc Health Risk Manage* 2016; 12:85-103].

Various treatment modalities for SDB have been recommended to reduce these vibrations. These techniques include preventive management, use of oral appliances, conservative treatment (continuous positive airway pressure (CPAP) devices), and surgery/laser assisted therapies [Ref s Fiz J A, Morera Prat J, Jane R (2009) *Treatment of patients with simple snoring. Arch Bronconeumol* 45:508-515]. Existing non-invasive methods are of limited use, e.g., they do not eliminate the cause of sleep apnea, are in-efficient, and are uncomfortable (e.g., such as in the case of CPAP devices). Moreover, the surgical procedures available today involve the need for local or general anesthesia and have the possibility of postoperative complications.

Another known technique for treating snoring is the use of laser therapy. Laser therapy has been shown to increase wound healing and collagen remodeling. In particular, the use of lasers in the treatment of snoring dates back to early 1990 when Kamami used a laser to perform laser-assisted uvulopalatoplasty (LAUP), which results in tissue reduction of the soft palate under local anesthesia. [Refs Kamami Y V (1990) *Laser CO$_2$ for snoring. Preliminary results. Acata Otorhinolaryngol Belg* 44:451-456]. However, Kamami's laser treatment always involved ablating or cutting the tissue for the purpose of removing swaths of tissue from a patient.

Recently, studies have shown that Er:YAG based lasers can help in reducing the severity of snoring and improve the quality of sleep without the need for anesthesia by tightening the soft palate tissue, mainly the oral mucosa. The tissue tightening is governed by two main principles: 1) collagen denaturation resulting in collagen shrinkage and tissue tightening and 2) wound healing response that generates new collagen and elastin. The oral mucosa consists of two layers: 1) surface stratified Squamous Epithelium and 2) the Lamina Propria which is made of a fibrous connective tissue laser that consists of a network of type I and III collagen and elastin fiber. Contraction occurs from the heat induced protein denaturation, dehydration of collagen above 60° C.

In particular, the use of laser energy at 2940 nm has been demonstrated to produce photothermal effect that results in shrinkage of collagen fibers in the pharyngeal and palatal soft tissues. [Ref Majaron B, Srinivas S M, He H, Nelson J S (2000) *Deep coagulation of dermal collagen with repetitive Er:YAG laser irradiation. Laser Surg Med* 26:215-222]. [Beltram M, Drnovsek-Olup B (2004) *Histological and biomolecular analysis of new collagen synthesis after "SMOOTH" mode Er; YAG laser skin resurfacing. Posters. Lasers Surg Med* 34:56]. Treatment with Er:YAG lasers typical entails three treatment sessions performed at 2 to 4 week intervals and are performed with a power of about 7 Watts, a typical fluence of about 2 J/cm$^2$, and about 15,000 pulses per treatment. A typical snoring prevention treatment session takes about 30-45 minutes.

Despite the advances made by Er:YAG laser treatments, there is still opportunity for significant improvement. For example, the 30-45-minute treatment time is long and can be onerous for patients needing to sit still in an operating chair during the procedure. Accordingly, a need exists for an improved laser-based treatment technique for treatment of soft tissue.

SUMMARY OF THE INVENTION

In view of the foregoing, it is desirable to provide an improved technique for soft tissue treatment, e.g., shrinking, tightening and increasing stiffness of the oral mucosa using an efficient, fast, anesthesia free procedure using a laser source. The present invention provides such a technique and relates to an improved laser-based treatment device for treatment of soft tissue that uses a laser source that operates in the 9 μm to 11 μm wavelength range, e.g., a CO$_2$ laser. CO$_2$ lasers have several advantages over Er:YAG lasers in soft tissue applications. For example, CO$_2$ lasers have an order of magnitude lower absorption coefficient than Er:YAG lasers in soft tissue which makes it more desirable for the treatment of soft tissue. Furthermore, CO$_2$ lasers have a deeper thermal effect into soft tissue (e.g., about 200 μm) than Er:YAG lasers and, therefore, have a greater capacity for collagen denaturation, thus requiring fewer treatment sessions a lower fluence (e.g., less than 0.2 J/cm$^2$). This results in less energy and surface damage and, as a result, a faster treatment time.

The present invention features a handpiece for directing radiation (e.g., a laser beam) in the near- to far-infrared spectra (e.g., 9-11 μm wavelength range), to allow for treatment of soft tissue in the oral cavity with optimal efficiency, minimal technique sensitivity, and a fast treatment time.

The system can be adapted to scan the laser beam using any known scanning technique, e.g., galvo-mirrors. The laser beam can be scanned across the treatment region using particular pattern(s) to allow for efficient energy delivery, producing enough localized photothermal effect to contract collagen without damaging (burning or charring) of the tissue. Such patterns are described in more detail in U.S. Patent Publication No. 20170319277, which is incorporated herein by reference in its entirety. In various embodiments, laser radiation provides enough energy to increase the biomechanical stiffness of the soft tissue such that it is fully contracted without further damage or charring of the tissue.

In some embodiments, the system includes a handpiece with an optical cartridge inserted inside that modifies the beam size to provide a different (larger or smaller) beam size than the original laser beam size. The optical cartridge enables the use of high power lasers in a non-ablative procedures by modifying the beam size using optical lenses mounted in the optical cartridge hence optimizing the fluence and/or energy density and further reducing the time of procedure.

Various aspects of the present invention include delivery of laser pulses with non-ablative energy levels to induce thermal heating on the surface of the pharyngeal and palatal soft tissue but does exceed a threshold value (e.g., about 65° C.).

The system may also include a laser source controller than can adjust one or more parameters of the radiation (e.g., laser pulse duration) according to the type of treatment selected and/or the type of tissue being treated. For example, during treatment, the laser beam may be directed to the treatment area, allowing for delivery of a specified energy profile at or near the treatment area.

In general, in one aspect, embodiments of the invention feature a system for contracting an area of soft tissue. The system can include a $CO_2$ laser source for generating a plurality of laser pulses of a laser beam having a wavelength in a range from 9 μm to 11 μm, a beam guidance system for directing the plurality of laser pulses to respective tissue locations within the soft tissue area, and a controller adapted to control the $CO_2$ laser source and the beam guidance system to achieve a therapeutically effective contraction of the soft tissue area at a rate of 1 $cm^2$ in no more than 25 seconds.

In various embodiments, each laser pulse has a fluence of no more than 0.2 $J/cm^2$ and/or a duty cycle in a range from 0.1 to 5 percent. The therapeutically effective contraction can include at least 10 percent of a full contraction of the soft tissue area. The beam guidance system can direct the plurality of laser pulses to respective tissue locations in a pattern. The pattern can have a number of locations (e.g., 15 to 1500 locations or 30 to 45 locations). The total pattern time can be in a range from 0.001 to 0.5 seconds. In some cases, the beam guidance system can repeat directing the plurality of laser pulses in the pattern to additional different soft tissue area portions, to achieve therapeutically effective contraction of all of the soft tissue area. The area of soft tissue can be located in a back of a throat and therapeutically effective contraction of all of the soft tissue area can be achieved during a total treatment time in a range from 3 to 20 min. In some cases, the pattern includes a first tissue location, at least one location non-adjacent to the first tissue location, and a location adjacent to the first tissue location. A quantity of the at least one non-adjacent location can be determined based at least in part on a thermal relaxation time of the soft tissue.

In various embodiments, the system can also include a handpiece forming an exit orifice and operatively connected to the beam guidance system for delivering the laser beam to the soft tissue area. In some cases, the exit orifice can direct the laser beam toward the soft tissue area along an exit axis substantially aligned with a longitudinal axis of the handpiece. The handpiece can also include a focusing optic and at least one lens (e.g., two lenses) disposed between the beam guidance system and the exit orifice. The focusing optic and the at least one lens can cooperate to increase a diameter of the laser beam (e.g., a collimated laser beam). In some instances, the laser beam has a working range (defined below) in a range from 1 cm to 5 cm.

In general, in another aspect, embodiments of the invention feature a method for contracting an area of soft tissue. The method can include the steps of generating a plurality of laser pulses of a laser beam having a wavelength in a range from 9 μm to 11 μm using a $CO_2$ laser source; and directing the plurality of laser pulses to respective tissue locations within the soft tissue area, such that a therapeutically effective contraction of the soft tissue area is achieved at a rate of 1 $cm^2$ in no more than 25 seconds.

In various embodiments, each laser pulse has a fluence of no more than 0.2 $J/cm^2$ and/or a duty cycle in a range from 0.1 to 5 percent. The therapeutically effective contraction can include at least 10 percent of a full contraction of the soft tissue area. The directing step can include directing the plurality of laser pulses to respective tissue locations in a pattern. The pattern can have a number of locations (e.g., 15 to 1500 locations or 30 to 45 locations). The total pattern time can be in a range from 0.001 to 0.5 seconds. In some cases, the directing step includes directing the plurality of laser pulses in the pattern to additional different soft tissue area portions, to achieve therapeutically effective contraction of all of the soft tissue area. The area of soft tissue can be located in a back of a throat and therapeutically effective contraction of all of the soft tissue area can be achieved during a total treatment time in a range from 3 to 20 min. In some cases, the pattern includes a first tissue location, at least one location non-adjacent to the first tissue location, and a location adjacent to the first tissue location. A quantity of the at least one location non-adjacent location can be determined based at least in part on a thermal relaxation time of the soft tissue. In some instances, the laser beam has a working range (defined below) in a range from 1 cm to 5 cm.

BRIEF DESCRIPTION OF THE DRAWINGS

In the drawings, like reference characters generally refer to the same parts throughout the different views. In the following description, various embodiments of the present invention are described with reference to the following drawings, in which:

FIG. 7 is a chart providing example laser and treatment parameter values, according to various embodiments.

DETAILED DESCRIPTION

Various embodiments of the present invention are directed to an improved laser treatment device that overcomes the shortcomings of conventional soft tissue treatment devices, e.g., with improved energy delivery, treatment time and number of treatments required to achieve effective therapeutic effect and without damaging the tissue or causing pain to the patient. The device can include a hand piece that delivers (i) laser pulses that heats the tissue without damage to therapeutically effective contraction, (ii) a laser beam having a long working range (defined below), and (iii) coolant (air, water, etc.) to an oral treatment region. The oral treatment area may include, for example: soft palate, uvula, palatine tonsils and the back of tongue; however, these are non-limiting examples. In general, any suitable tissue region can be treated.

Figure 1A:
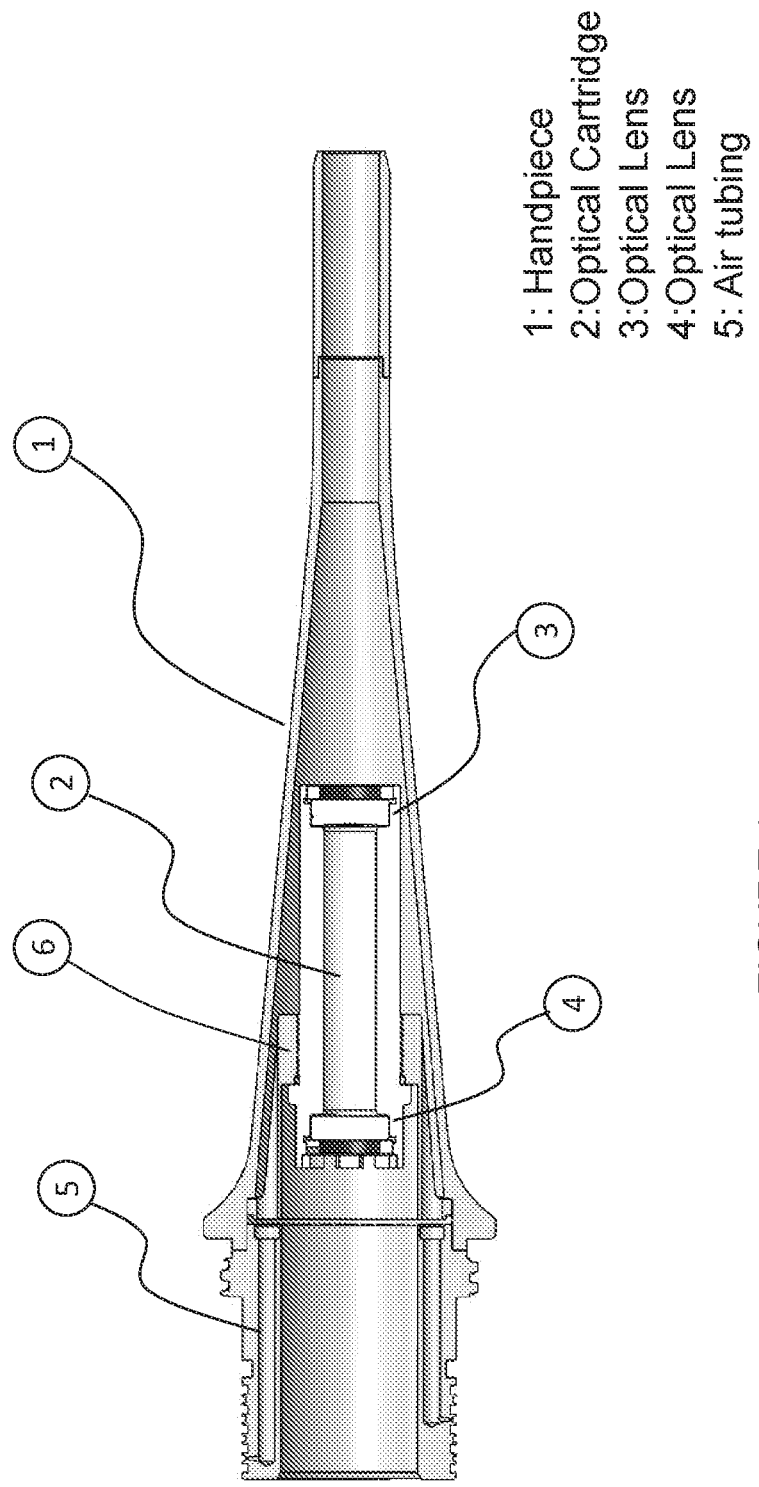
FIG. 1A is a side cross-sectional schematic view of a straight handpiece and optical cartridge, according to various embodiments.
Figure 1B:
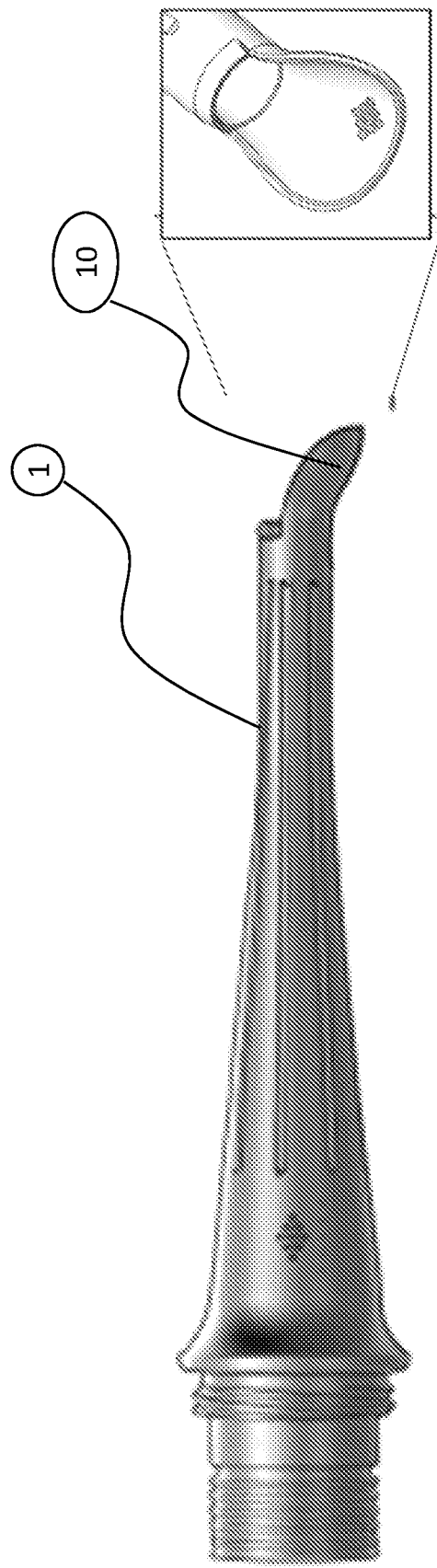
FIG. 1B is a side cross-sectional schematic view of a straight handpiece including a tongue depressor, according to various embodiments.

For some applications, a $CO_2$ laser source operating at a wavelength in a range of 9-11 µm (e.g., 9.3 µm, 10.6 µm), is desirable for such treatments. For example, $CO_2$ lasers can be delivered using a handpiece 1. As shown in FIG. 1A, the handpiece can have a straight configuration that can enable access to challenging locations in the mouth. In some cases, as shown for example in FIG. 1B, the handpiece can include an integrated tongue depressor 10. The handpiece 1 can accomplish treatment efficiently and with a fast treatment time and without need for anesthesia. Some advantages of the laser therapy described herein over conventional methods include increased collagen contraction and regeneration that leads to increased tissue stiffness with minimal pain or sensation. Furthermore, treatment of the affected area using the laser therapy described herein has a longer lasting effect (e.g., contraction of the tissue lasts for a longer time) than conventional techniques, which can reduce the number of treatments needed (e.g., less than 2, 3, 4, 5, or 6 treatments per year).

The laser is pulsed and scanned in a certain pattern to allow optimal collagen contraction of the oral mucosa and other soft tissue and minimal heat accumulation. In some embodiments, the delivery of a collimated laser beam is achieved by a handpiece 1, which may be structured and designed to receive an optical cartridge 2. The optical cartridge 2 can include at least one optical lens to modulate a laser beam passing therethrough. For example, as shown in FIG. 1A, the optical cartridge can include an upstream optical lens 3 and a downstream optical lens 4. The optical cartridge 2 can be mounted to the handpiece 1 using any known technique, e.g., with a threading 6. The ability to replace or remove the optical cartridge 2 allows switching the laser between treatment modes, such as an ablative mode to a non-ablative mode and vice versa. In addition, tubing 5 in the handpiece may be used to deliver cooling fluids (e.g., air, water, and combinations thereof) to provide cooling of the tissue surface and avoid any contaminants from reaching the optics. The tubing 5 can be sealed using known techniques.

Figure 2:
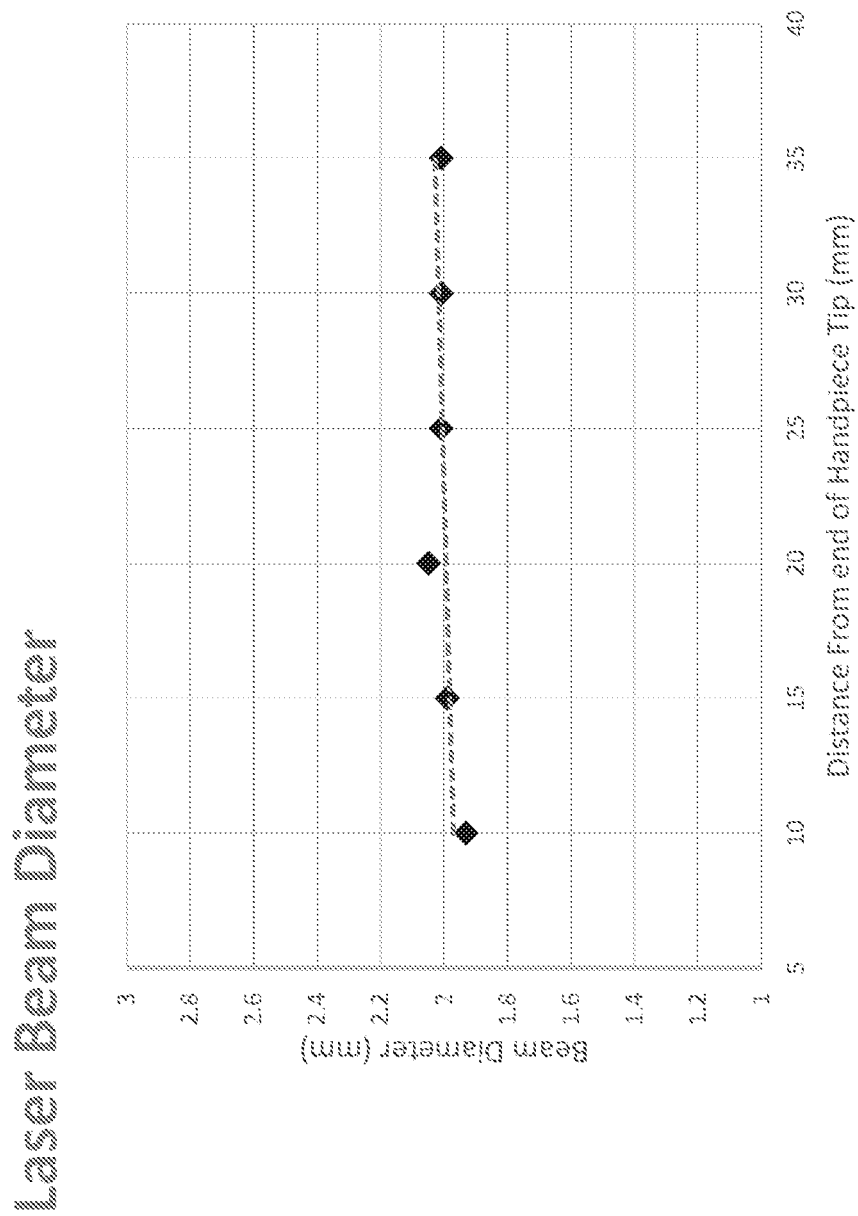
FIG. 2 is an example plot of a beam size diameter that defines a working range of the native beam where the beam is collimated, according to various embodiments.

In addition, the optical cartridge 2 can provide a laser beam having a long working range. As used herein the term "working range" means the distance along the length of the laser beam at which the laser beam has a fluence capable of treating the tissue (e.g., capable of fully contracting the tissue). Conventional devices have a relatively short working range, typically focused tightly around the focal point of the laser beam, out of a desire to not waste any energy along the length of the laser. The laser treatment device of the present invention can, in some embodiments, tolerate a longer working range, so as to enable an operator to move his/her hand (and, corresponding, the laser beam), while still treating the treatment area. The concept of a working range is described in more detail with reference to the phrase "depth of treatment" (which can be interchanged with "working range") in U.S. Patent Publication No. 20160143703, which is incorporated by reference herein in its entirety. In other words, in certain embodiments, the amount of energy on the target tissue does not change over a relatively long distance (e.g., more than 0.5 cm, more than 1 cm, more than 1.5 cm, more than 2 cm, more than 3 cm, more than 4 cm) to accommodate for hand movements and variability in the user's holding of the handpiece and to accommodate for human factors. FIG. 2, for example, is a plot showing exemplary beam diameter measurements at a distance from an end of the handpiece 1. As shown, in this example, the beam diameter does not change over a range of 25 mm.

In various embodiments, laser parameters (e.g., shown in FIG. 7, power, repetition rate, pulse duration, and/or laser beam overlap) may be selected to optimize efficiency and to contact tissue without damage. Moreover, the laser source may be spatially scanned to provide different pulse energies at different locations.

Figure 3:
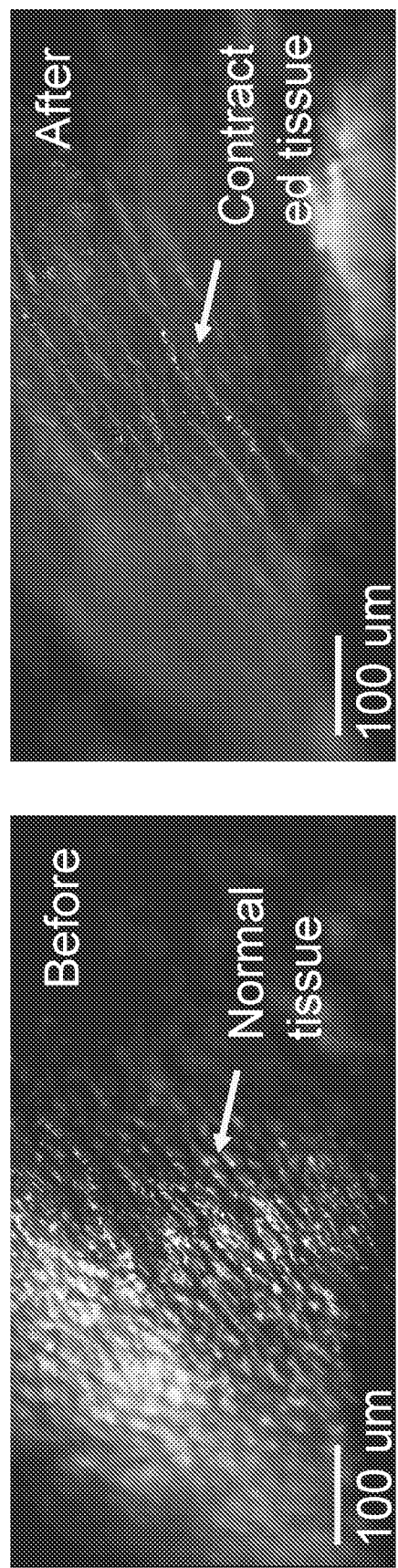
FIG. 3 is a microscope image illustrating soft tissue shrinkage in chicken skin before and after laser irradiation, according to various embodiments.

FIG. 3 shows two microscope images of chicken tissue before and after lasing with the $CO_2$ laser. The features on the surface of the tissue are contracted closer together as a result of heat induced contraction throughout the tissue. The cross linking between collagen fibrils are disrupted resulting in a collapse of collagen fibrils into a lower entropy state.

For an efficient treatment, contraction of the soft tissue without damage or charring is desirable. One of the major mechanisms underlying the clinical effect of tissue tightening is a structural change in the collagen polymer induced by thermal energy, causing collagen shrinkage. Collagen is the most abundant protein in soft tissue and it is a polymer that exists as a triple helix with chains held together by hydrogen bonds. When enough thermal energy is delivered to collagen, there is denaturation of the collagen triple helix into a haphazard coil pattern. The heat-stable intermolecular cross-links are maintained within the new collagen configuration which leads to increased tension within the collagen as the structure shrinks and thickens. Thermal treatment of tissues triggers a wound healing response, which includes three phases. In the first proliferation phase Collagen I-III is produced; in the second phase, fibroblasts differentiate into myofibroblasts and cause tissue contraction; and in the third remodeling phase, the tissue becomes more compact and there is an increase in collagen. Heat-induced collagen denaturation depends on both the amount of thermal power delivered (see FIG. 4a) and the amount of time of thermal treatment (see FIG. 4b). If too much thermal power is delivered to the tissue, a damage threshold is exceeded and the tissue is ablated, burned, or charred. As used herein, the damage threshold refers to any combination of laser treatment parameters that causes the tissue to ablate, burn, or char. As used herein, in one embodiment, the term full contraction refers to contraction of the tissue within a predetermined percentage of the damage threshold, which in some cases can be the contraction of the tissue at the damage threshold, generally as a function of at least one of power and lasing time. The predetermined percentage within which full contraction is of the damage threshold can be, in various embodiments, in a range from 25%-0.01%, in a range from 20%-1%, in a range from 15%-3%, and in a range from 10%-5% (e.g., 25%, 20%, 15%, 10%, 7%, 5%, 3%, 1%, 0.5%, 0.3%, 0.1%, 0.07%, 0.05%, 0.03%, and 0.01%). In certain commercial applications, tissue will only be contracted to within a certain safety margin of the damage threshold, to avoid potential harm or discomfort to the patient.

As used herein, the term therapeutically effective contraction refers to an amount of contraction that is a predetermined percentage of full contraction. The predetermined percentage of full contraction can be, in various embodiments, in a range from 5% to 100%, in a range from 10% to 95%, in a range from 15% to 90%, in a range from 20% to 85%, in a range from 25% to 80%, in a range from 30% to 75%, in a range from 35% to 70%, in a range from 40% to 65%, in a range from 45% to 60%, and in a range from 50% to 55%. As examples, in various embodiments, the predetermined percentage of full contraction can be: at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, and at least 99%. In general, therapeutically effective contraction results in a reduction of snoring that lasts for a therapeutically and commercially effective period of time (e.g., a week, several weeks, a month, several months, a year, several years, or longer).

Figure 4B:
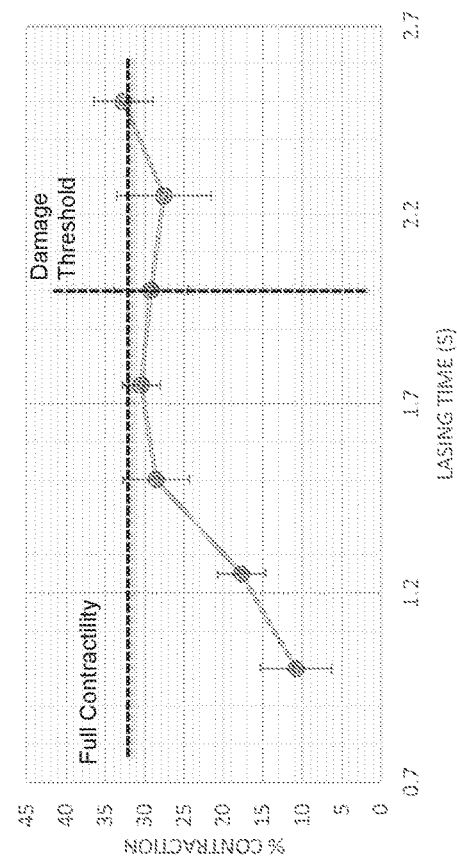
FIGS. 4a-4b are example plots of percentage collagen contraction to full contraction as a function of power and lasing time, respectively, according to various embodiments.
Figure 4A:
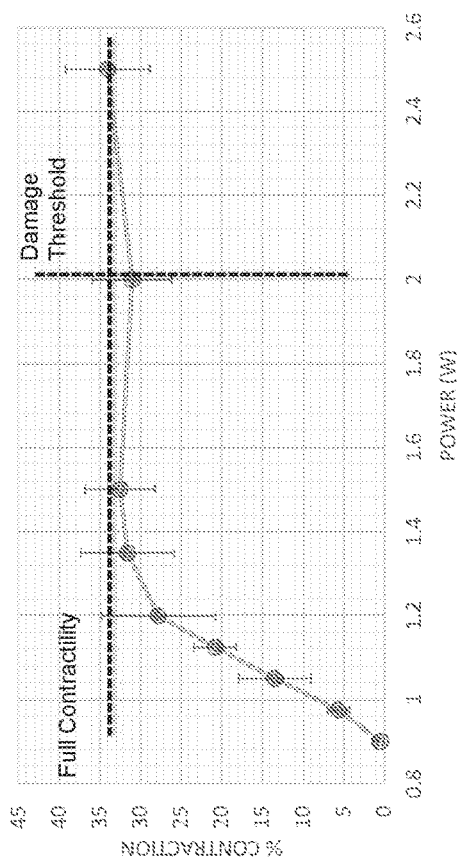

FIG. 4a is a plot with example data showing the effect of laser radiation power on percentage contraction. In this example, an optimal average power irradiation of 1.5 Watts can result in full contraction while remaining below the damage threshold. However, in other embodiments with, e.g., different operating conditions or laser parameters, different average power amounts can be used. For example, average power can be in a range from 0.1 Watts to 5 Watts, 0.5 Watts to 4.5 Watts, 1 Watt to 4 Watts, 1.5 Watts to 3.5 Watts, and 2 Watts to 3 Watts. In various embodiments, average power can be about 0.5 Watts, 1 Watt, 1.5 Watts, 2 Watts, 2.5 Watts, 3 Watts, 3.5 Watts, 4 Watts, 4.5 Watts, and 5 Watts. FIG. 4b is a plot with example data showing the effect of lasing time on percentage contraction at a single treatment location. In this example, an optimal lasing time of about 1.8 seconds can result in full contraction of a 1 $cm^2$ tissue portion while remaining below the damage threshold. However, in other embodiments with, e.g., different operating conditions or laser parameters, different lasing times can be used. For example lasing time can be in a range from 0.1 seconds to 2 minutes, 1 second to 90 seconds, 5 seconds to 60 seconds, 7 seconds to 55 seconds, 9 seconds to 50 seconds, 11 seconds to 45 seconds, 13 seconds to 40 seconds, 15 seconds to 35 seconds, 17 seconds to 30 seconds, 20 seconds to 25 seconds, 0.1 seconds to 5 seconds, 0.5 seconds to 4.5 seconds, 1 second to 4 seconds, 1.5 seconds to 3.5 seconds, and 2 seconds to 3 seconds. In various embodiments, lasing time can be no more than 0.5 seconds, no more than 1 second, no more than 1.5 seconds, no more than 1.6 seconds, no more than 1.7 seconds, no more than 1.8 seconds, no more than 1.9 seconds, no more than 2 seconds, no more than 2.5 seconds, no more than 3 seconds, no more than 3.5 seconds, no more than 4 seconds, no more than 4.5 seconds, no more than 5 seconds, no more than 7 seconds, no more than 10 seconds, no more than 15 seconds, no more than 20 seconds, no more than 25 seconds, no more than 30 seconds, no more than 40 seconds, no more than 50 seconds, no more than 1 minute, no more than 90 seconds, no more than 2 minutes.

Figure 4C:
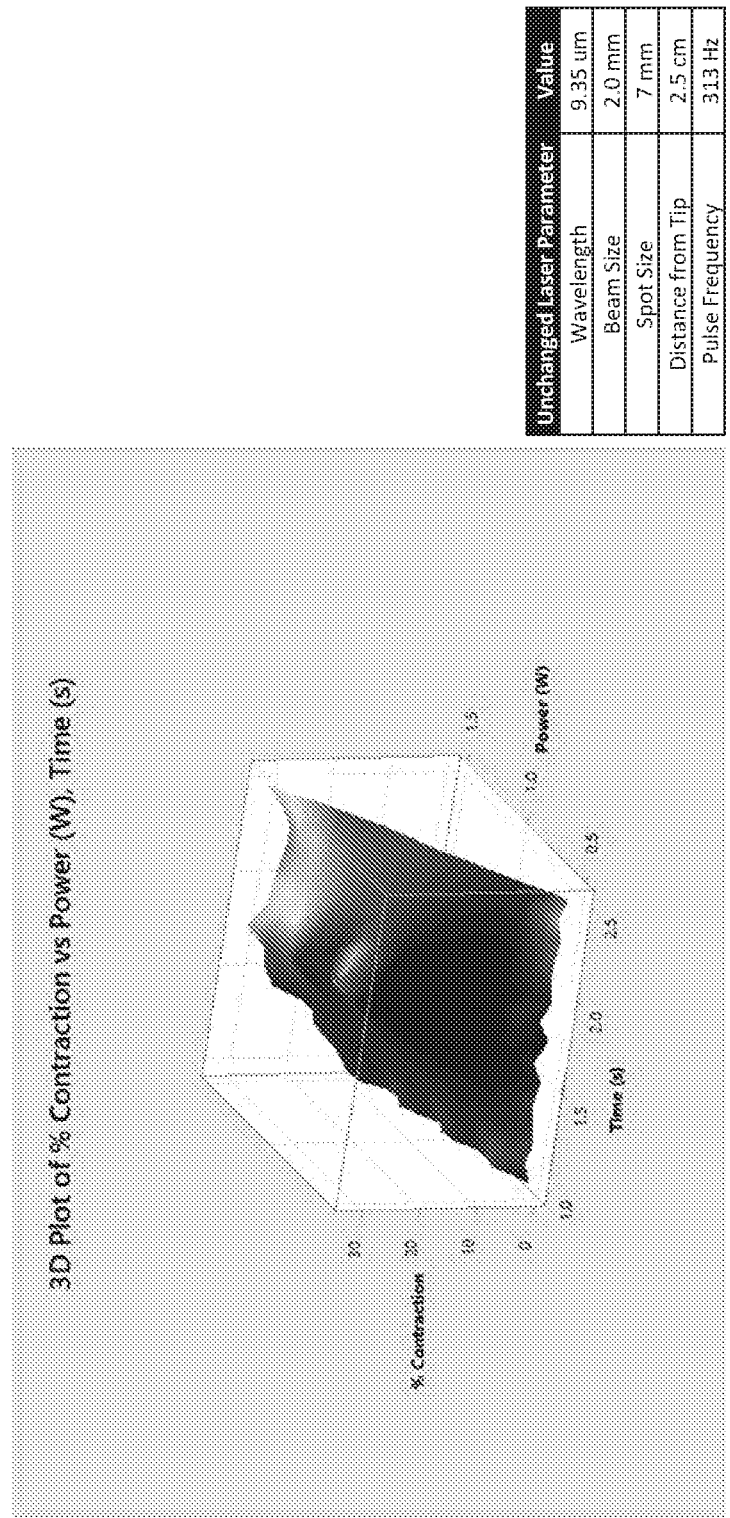
FIG. 4c is an example 3D plot combining the data shown in FIGS. 4a and 4b.

The above lasing times are example lasing time ranges for the treatment of a 1 $cm^2$ portion of soft tissue. However, as used in this application, this disclosure should be interpreted as support for a rate of treatment, meaning the disclosed lasing times are the amount of time it would take to treat a 1 $cm^2$ portion, but that rate of treatment can be used to treat a smaller or larger area. As one example, the disclosure of a lasing time of no more than 25 seconds should be interpreted as support for treating at a rate of 1 $cm^2$ in no more than 25 seconds. This rate of treatment can be extrapolated down or up to determine an amount of time required to treat a smaller area, e.g., 1 $mm^2$ in 0.25 seconds or a larger area, e.g., 10 $cm^2$ in 250 seconds. Moreover, even though the rate of treatment is expressed as a unit of 2-dimensional area per measure of time, in various embodiments, the supported rates of treatment can be used to treat any portion of the soft tissue, including 2-dimensional and 3-dimensional portions, using conventional geometric and mathematical conversion techniques. For example, the supported rates of treatment can be used to treat discrete points, lines (linear and non-linear), circle perimeters, volumes, and any other portion of the soft tissue. FIG. 4c is a 3D plot combining the data shown in FIGS. 4a and 4b. The other laser parameters that were held constant as time and power were varied are shown in a chart on FIG. 4c.

In various embodiments, a therapeutically effective contraction can be achieved by operating the laser such that a predetermined number of pulses are delivered during a predetermined period of time sufficient to accomplish the therapeutically effective contraction. For example, laser pulses can be delivered at the following rates: a sequence of 15 pulses in a range of 0.1 msec to 49 msec, 1 msec to 45 msec, 2 msec to 40 msec, 3 msec to 35 msec, 4 msec to 30 msec, 5 msec to 25 msec, 6 msec to 20 msec, 7 msec to 15 msec, and 8 msec to 10 msec. The preceding description provides support for various rates of treatment (secs/pulse) and can be extrapolated up or down for the delivery of any number of pulses using known mathematical techniques. In some cases, the extrapolation can be based on equal time spacing between pulses (e.g., 15 pulses in 49 msec is a rate of 3.3 msec per pulse). In another example embodiments, laser pulses can be delivered at a rate of 37 pulses in 0.118 sec (or 3.2 msec per pulse). In other cases, the extrapolation can be based on different time spacing between the pulses.

Irradiation of soft tissue with a lower power level laser results in increased stiffness and contraction. For example, an animal study was conducted to measure these characteristics. The animal study included two different groups of rats. A lased group, which was irradiated with a laser, and a control group, which was not exposed to any laser irradiation. The irradiation of the lased group was performed in one session with an average $CO_2$ laser power of 1.5 Watts over a period of 10 seconds per rat. The fluence was about 0.16 $J/cm^2$ achieved by a native beam diameter of 2 mm ($1/e^2$) measured by knife edge technique. The native beam was scanned in a certain pattern with specific parameters, e.g., a combination of those listed in FIG. 7, as for example. The size of the pattern was 7 mm, which was chosen in part because it was large enough to visualize a change of the target tissue.

Figure 5:
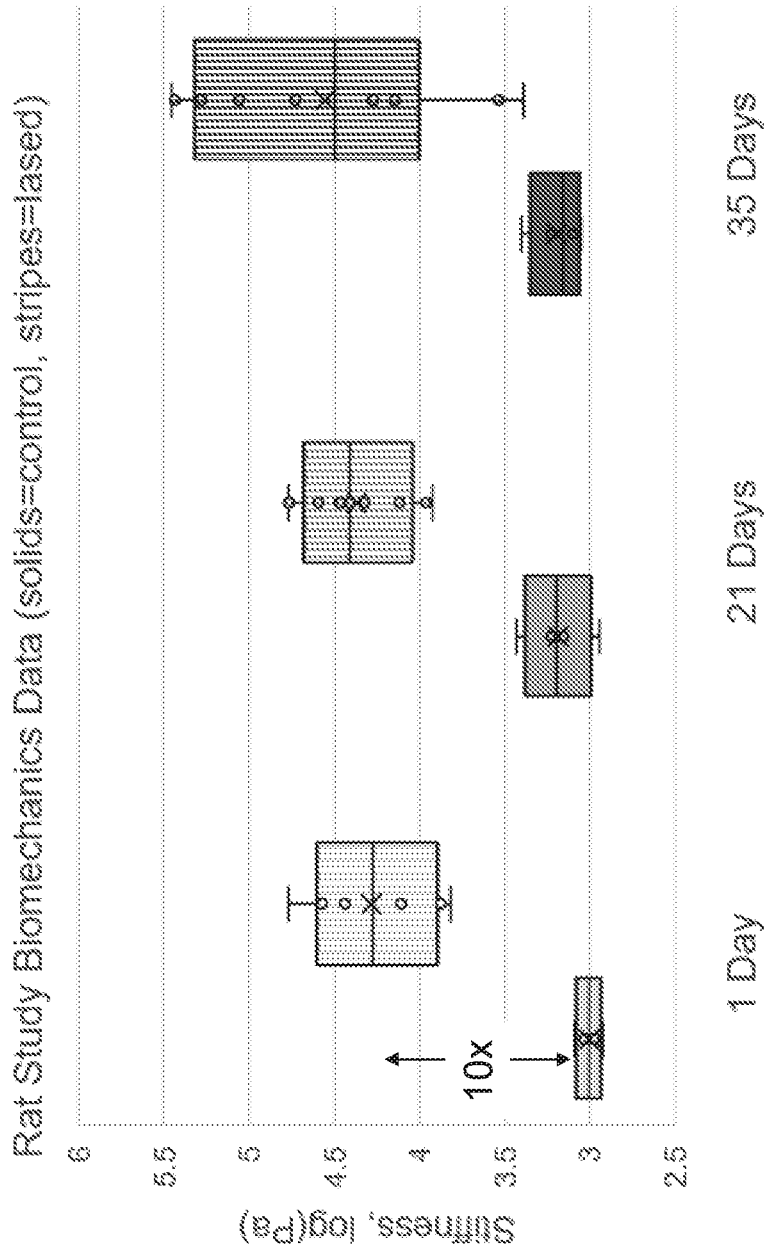
FIG. 5 is an example plot of biomechanics data of the measured stiffness of excised rat tissues of the lased group and compared to the control group in an animal study, according to various embodiments.

Collagen shrinkage (contraction) and biomechanical tissue stiffness were measured at three different time points, 24 hours, 21 days and 35 days after the irradiation session for each of the lased (n=10) and control groups (n=5). At each of the time points, a section of the soft palate was excised and divided into two samples, one section to obtain histology data to quantify collagen denaturation and another section to obtain stiffness data to quantify biomechanics characteristics by measuring the Young's modulus (KPa). FIG. 5 shows the stiffness results of the excised tissue, from both the lased and control groups, at the three time points mentioned above. As shown, the lased group exhibited a tenfold increase in stiffness at each time point over the control group. In this example experiment, the mean stiffness values for the control groups were 1.0±0.17 kPa at day 1, 1.7±0.17 kPa at day 21, and 1.6±0.63 kPa at day 35. No significant difference was found between the three control groups ($p>0.05$). The mean stiffness values for the treatment groups were 25±18 kPa for day 1, 29±19 kPa for day 21, and 97±113 kPa for day 35. No significant difference was found between the three treated groups ($p>0.05$). The increase in stiffness of the treated animal tissues was maintained at over an order of magnitude over that of the controls ($p<0.002$ for each time point). These data are one example of achievable results. In various embodiments, laser treatment of the soft tissue as described herein can result in a stiffness increase of the tissue in a range from 1.1-fold to 250-fold, 1.1-fold to 100-fold, 1.5-fold to 95-fold, 2-fold to 90-fold, 5-fold to 85-fold, 7-fold to 80-fold, 10-fold to 70-fold, 12-fold to 60-fold, 15-fold to 40-fold, and 20-fold to 30-fold. For example, laser treatment can result in a stiffness increase of the tissue of at least 2-fold, at least 5-fold, at least 10-fold, at least 15-fold, at least 20-fold, at least 25-fold, at least 30-fold, at least 40-fold, at least 50-fold, at least 60-fold, at least 70-fold, at least 80-fold, at least 90-fold, at least 100-fold, and at least 250-fold. In various embodiments, soft tissue that undergoes laser treatment as described herein can, over the period in a range from 2 weeks to 6 weeks (e.g., 1 month), undergo an increase in stiffness in a range from 1.1-fold to 10-fold, 2-fold to 9-fold, 3-fold to 8-fold, 4-fold to 7-fold, and 5-fold to 6-fold. For example, laser treatment can result in a stiffness increase of the treated tissue of at least 1.1 fold, at least 1.5-fold, at least 2-fold, at least 3-fold, at least 4-fold, at least 5-fold, at least 6-fold, at least 7-fold, at least 8-fold, at least 9-fold, and at least 10-fold.

The measured increase in stiffness over the 2 week to 6 week range confirms that the soft tissue biomechanical changes persist into the remodeling phase, which can be based on the duration of the fibrosis or otherwise altered collagen structure according to the wound healing process. Therefore, the increased stiffness can be maintained for significantly longer periods without significant deterioration. For example, in various embodiments, the stiffness values can decrease by in a range of 0.1% to 30%, 2% and 25%, 3% and 20%, 4% and 15%, and 6% and 10%, e.g., less than 30%, less than 25%, less than 20%, less than 15%, less than 10%, less than 5%, and less than 1% over any of the following time periods following the increase in stiffness measured in the range of 2 weeks to 6 weeks following treatment: at least 1 month, at least 3 months, at least 6 months, at least 9 months, at least 12 months, at least 15 months, at least 18 months, at least 21 months, and at least 24 months.

Figure 6:
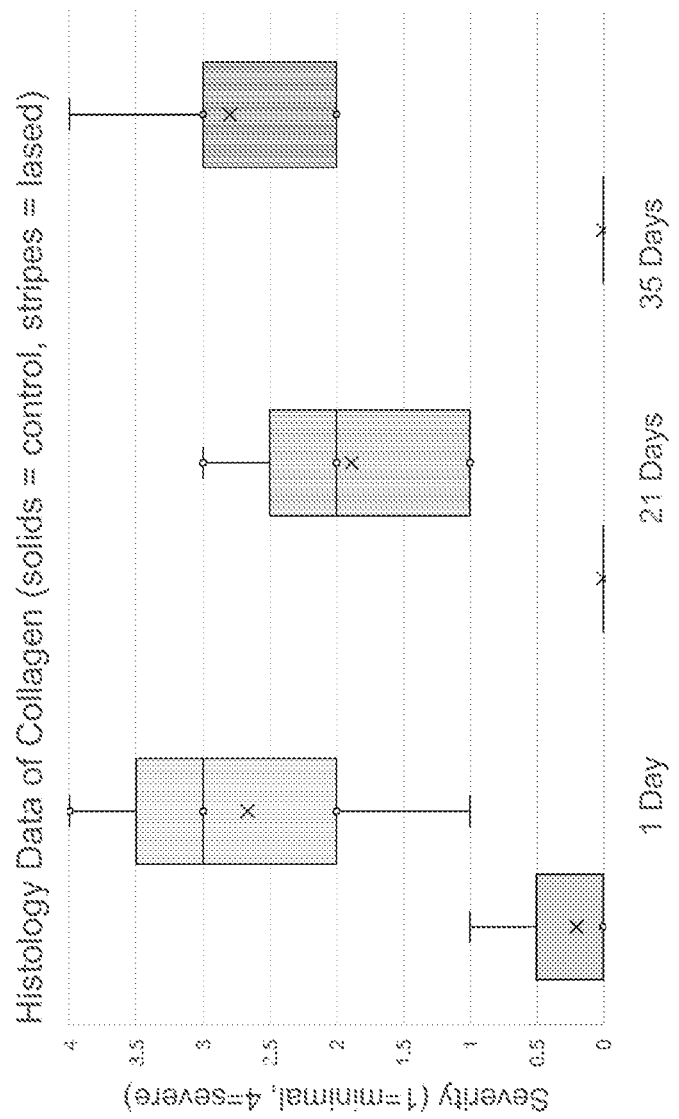
FIG. 6 is a plot of histology data of collagen contraction of excised rat tissues of the lased group and compared to the control group in an animal study, according to various embodiments.

Similarly, the histology data show increased collagen shrinkage for the lased group and remains higher than that of control over the three time points, as shown in FIG. 6. In this example experiment, the mean collagen histopathological values for control groups were 0.20±0.45 for day 1 and 0 for days 21 and 35. No significant difference was found between the three control groups ($p>0.05$). The mean collagen histopathological values for the lased groups were 2.7±1.0 for day 1, 1.9±0.78 for day 21, and 2.8±0.63 for day 35. No significant difference was found between the three treated groups ($p>0.05$). An overall change from baseline persisted through the inflammation stage (day 1) and into the tissue remodeling stages (days 21 and 35). These data are one example of achievable results. In various embodiments, laser treatment of the soft tissue as described herein can result in a histopathological value increase of the tissue in a range from 1.1-fold to 250-fold, 1.1-fold to 100-fold, 1.1-fold to 50-fold, 1.5-fold to 47-fold, 2-fold to 45-fold, 4-fold to 43-fold, 6-fold to 40-fold, 8-fold to 35-fold, 10-fold to 30-fold, 12-fold to 25-fold, and 14-fold to 20-fold. For example, laser treatment can result in a histopathological value increase of the tissue of at least 2-fold, at least 4-fold, at least 6-fold, at least 8-fold, at least 10-fold, at least 12-fold, at least 14-fold, at least 20-fold, at least 25-fold, at least 30-fold, at least 35-fold, at least 40-fold, at least 45-fold, at least 50-fold, at least 100-fold, and at least 250-fold. In various embodiments, soft tissue that undergoes laser treatment as described herein can, over the period in a range from 2 weeks to 6 weeks (e.g., 1 month), undergo an increase in histopathological value in a range from 1.02-fold to 10-fold, 1.05-fold to 9-fold, 1.1-fold to 8-fold, 1.5-fold to 7-fold, 2-fold to 6-fold, 3-fold to 5-fold, 1.02-fold to 1.1-fold, 1.03-fold to 1.09-fold, 1.04-fold to 1.08-fold, and 1.05-fold to 1.07-fold. For example, laser treatment can result in a stiffness increase of the treated tissue of at least 1.02-fold, at least 1.04-fold, at least 1.06-fold, at least 1.08-fold, at least 1.1-fold, at least 1.2-fold, at least 1.3-fold, at least 1.5-fold, at least 2-fold, at least 3-fold, at least 4-fold, at least 5-fold, at least 6-fold, at least 7-fold, at least 8-fold, at least 9-fold, and at least 10-fold. The measured increase in histopathological value over the 2 week to 6 week range confirms that the soft tissue biomechanical changes persist into the remodeling phase, which can be based on the duration of the fibrosis or otherwise altered collagen structure according to the wound healing process. Therefore, the increased histopathological value can be maintained for significantly longer periods without significant deterioration. For example, in various embodiments, the stiffness values can decrease by in a range of 0.1% to 30%, 2% and 25%, 3% and 20%, 4% and 15%, and 6% and 10%, e.g., less than 30%, less than 25%, less than 20%, less than 15%, less than 10%, less than 5%, and less than 1% over any of the following time periods following the increase in histopathological value measured in the range of 2 weeks to 6 weeks following treatment: at least 1 month, at least 3 months, at least 6 months, at least 9 months, at least 12 months, at least 15 months, at least 18 months, at least 21 months, and at least 24 months. [Ref Von Den Hoff J. W., Maltha, J. C., Kniipers-Jastman A. M. (2006) *Palatal Wound Healing: The Effects of Scarring on Growth*. In: Berkowitz S. (eds) *Cleft Lip and Palate*. Springer, Berlin, Heidelberg, https://doi.org/10.1007/3-540-30020-1_201].

The measured increase in stiffness and/or histopathological value between 21 days and 35 days is important because it indicates the formation of new collagen during the proliferation phase of the wound healing process. In addition, the measured results indicate that the increased stiffness of the tissue, caused initially by the contraction/disruption of collagen, persisted through the inflammatory phase and into the tissue remodeling phase, rather than softening or breaking down as the tissue changed structure. Over time, collagen was recruited, causing a thickening of the lamina propria, which was indicative of a maturing fibrosis. This means that the effect can last for several months and up to 1-2 years or more. [Ref F Wherhan, S Schultze-Mosgau, H Schliephake "*Salient Features of the Oral Mucosa*" Essential Tissue Healing of the Face & Neck]. The fibrosis-like formation may be the desired result to provide a lasting benefit in the reduction of snoring vibrations.

In some variations, radiation emitted by a laser source may be transmitted through the handpiece 1 accompanied by mist and/or air. The cooling is carried through tubings 5 that run along the handpiece 1 and circumvent the optical cartridge 2. The cooling might be useful to reduce any unintentional heating of the tissue, as for example, if the handpiece 1 dwells for a long time at the same location and is not moved along the back of the throat.

In certain embodiments, the $CO_2$ laser is accompanied with a marking beam (e.g., green in color) that serves as a guidance of the location of the laser beam on the target tissue. In other embodiments, the irradiation of the laser may consist of a pattern. A visual or sonar feedback can be integrated within the system to indicate to the user the need to move to a new target area. A visual feedback to move for a new target area can include a stationary guidance beam (e.g., a green point can be seen on the tissue). For example, while the tissue is being exposed to the laser, a pattern is displayed on the tissue. When enough dose of energy has been delivered in a pattern to contract collagen, the laser can stop scanning and a point object can be projected on the target tissue. Alternatively, a sonar feedback can include a sound emerging from the system when the sequence of patterns or energy dose is delivered.

FIG. 7 is a chart including exemplary laser and operation parameters. Laser parameters (e.g., power, repetition rate, pulse duration, and laser beam overlap) may be designed to have an optimal outcome of efficiency to remove diseased tissue or bone without damaging the material (i.e., optical cartridge 2) itself. However, the laser source may be spatially scanned to provide different pulse energy at different locations, as will be appreciated by those skilled in the art.

Figure 8:
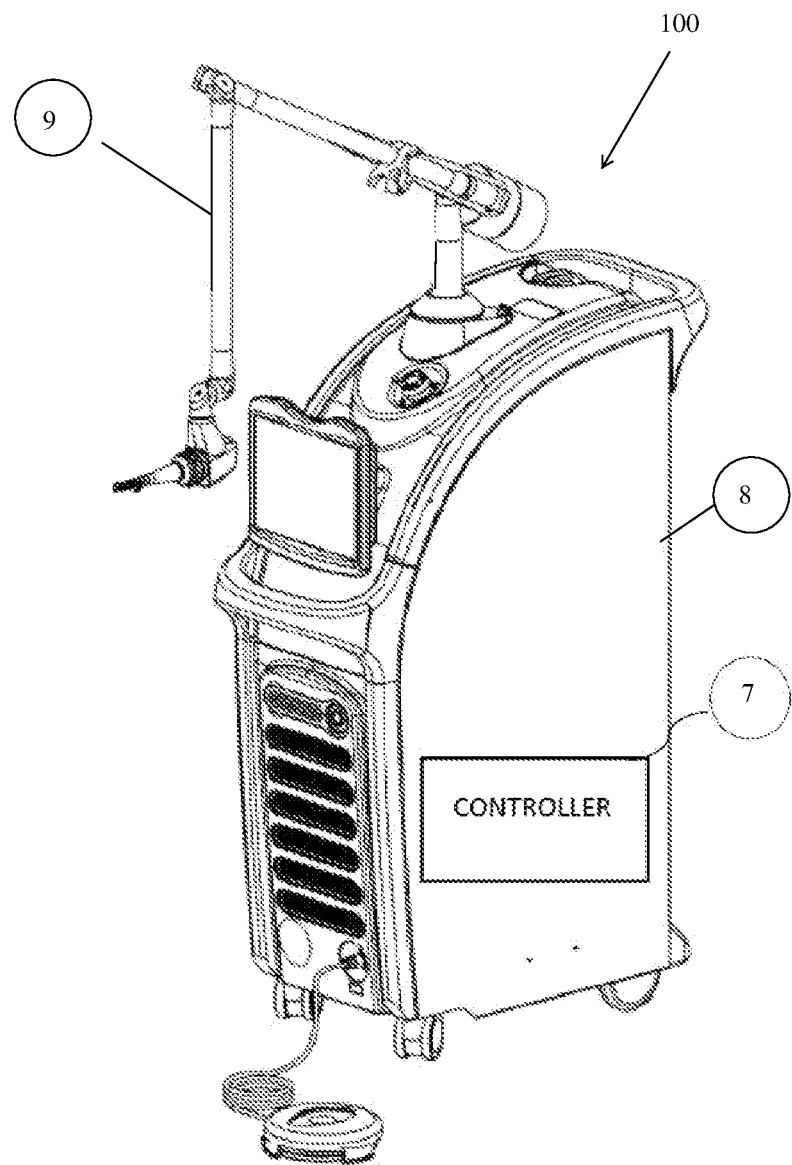
FIG. 8 is a schematic perspective view of a dental laser system, according to various embodiments.

FIG. 8 is a schematic depiction of an exemplary laser treatment system 100 that can be used for the laser treatments described in this application. As shown, in some embodiments the treatment system 100 can include a laser source 8 and a beam guidance system 9. The system can also include a controller 7 for controlling both the laser source 8 and the beam guidance system 9. Additional details on the laser treatment system 100 can be found in US Patent Publication No. 2014/0363784A1, which is incorporated by reference herein in its entirety.

Each numerical value presented herein is contemplated to represent a minimum value or a maximum value in a range for a corresponding parameter. Accordingly, when added to the claims, the numerical value provides express support for claiming the range, which may lie above or below the numerical value, in accordance with the teachings herein. Every value between the minimum value and the maximum value within each numerical range presented herein (including in the chart shown in FIG. 7), is contemplated and expressly supported herein, subject to the number of significant digits expressed in each particular range.

Having described herein illustrative embodiments of the present invention, persons of ordinary skill in the art will appreciate various other features and advantages of the invention apart from those specifically described above. It should therefore be understood that the foregoing is only illustrative of the principles of the invention, and that various modifications and additions can be made by those skilled in the art without departing from the spirit and scope of the invention. Accordingly, the appended claims shall not be limited by the particular features that have been shown and described but shall be construed also to cover any obvious modifications and equivalents thereof.

What is claimed is:

1. A system for contracting at least one soft tissue location, the system comprising:
a $CO_2$ laser source for generating a plurality of laser pulses of a laser beam, wherein the laser pulses have a wavelength in a range from 9 µm to 11 µm;
a beam guidance system for directing the plurality of laser pulses to the at least one soft tissue location; and
a controller adapted to control the $CO_2$ laser source and the beam guidance system to achieve a predetermined percentage of full contraction of the at least one soft tissue location that occurs at a damage threshold of the at least one soft tissue location, wherein the predetermined percentage of full contraction comprises 20 percent of full contraction achieved at a rate of 1 $cm^2$ in no more than 15 seconds.

2. The system of claim 1, wherein the predetermined percentage of full contraction comprises 20 percent of full contraction achieved at a rate of 1 $cm^2$ in no more than 10 seconds.

3. The system of claim 1, wherein the laser beam has a working range having a length in a range from 1 cm to 5 cm.

4. The system of claim 1, wherein each laser pulse is delivered at a rate of up to 3.3 msec per pulse.

5. The system of claim 1, wherein each laser pulse has a fluence of no more than 0.2 $J/cm^2$.

6. The system of claim 1, wherein each laser pulse comprises a duty cycle in a range from 0.15 to 5%.

7. The system of claim 1, wherein the beam guidance system is adapted to direct the plurality of laser pulses each of the at least one soft tissue location in a pattern.

8. The system of claim 7, wherein the pattern comprises a total pattern time in a range from 0.01 second to 0.5 second.

9. The system of claim 7, wherein the beam guidance system is adapted to repeat directing the plurality of laser pulses in the pattern to additional different soft tissue area portions, to achieve the predetermined percentage of full contraction of all of the soft tissue area portions.

10. The system of claim 7, wherein the pattern comprises a first tissue location, at least one location non-adjacent to the first tissue location, and a location adjacent to the first tissue location.

11. The system of claim 10, wherein a quantity of the at least one location non-adjacent location is determined based on a thermal relaxation time of the soft tissue.

12. The system of claim 1 further comprising a handpiece forming an exit orifice and operatively connected to the beam guidance system for delivering the laser beam to the at least one soft tissue location.

13. The system of claim 12, wherein the handpiece further comprises a focusing optic and at least one lens disposed between the beam guidance system and the exit orifice.

14. The system of claim 13, wherein the at least one lens comprises two lenses.

15. The system of claim 13, wherein the focusing optic and the at least one lens are structured and arranged to generate a collimated laser beam.

16. The system of claim 13, wherein the focusing optic and the at least one lens are structured and arranged to increase a diameter of the laser beam.

17. A method for contracting at least one soft tissue location, the method comprising the steps of:
generating a plurality of laser pulses of a laser beam;

directing the plurality of laser pulses to the st least one soft tissue location; and achieving a predetermined percentage of full contraction of the at least one soft tissue location occurring at a damage threshold of the at least one soft tissue location.

18. The method of claim 17, wherein the laser pulses have a wavelength in a range from 9 μm 11 μm.

19. The method of claim 17, wherein the predetermined percentage of full contraction of the at least one soft tissue location comprises 20 percent of full contraction achieved at a rate of 1 cm$^2$ in no more than 15 seconds.

20. A system for contracting at least one soft tissue location, the system comprising:

a laser source for generating a plurality of laser pulses of a laser beam;

a beam guidance system for directing the plurality of laser pulses to the at least one soft tissue location; and a controller adapted to control the laser source and the beam guidance system to achieve 20 percent of full contraction of the at least one soft tissue location at a rate of 1 cm$^2$ in no more than 15 seconds, wherein full contraction occurs at a damage threshold of the at least one soft tissue location.

* * * * *